United States Patent [19]

Gries

[11] 4,269,819
[45] May 26, 1981

[54] 2,4,6-TRIIODOBENZONITRILE DERIVATIVES AND X-RAY CONTRAST MEDIA COMPRISING THEM

[75] Inventor: Heinz Gries, Berlin, Fed. Rep. of Germany

[73] Assignee: Schering Aktiengesellschaft, Berlin and Bergkamen, Fed. Rep. of Germany

[21] Appl. No.: 57,243

[22] Filed: Jul. 12, 1979

[30] Foreign Application Priority Data

Jul. 14, 1978 [DE] Fed. Rep. of Germany ....... 2831496
Jan. 19, 1979 [DE] Fed. Rep. of Germany ....... 2902456

[51] Int. Cl.³ .................... A61K 49/04; C07C 121/52
[52] U.S. Cl. .................................... 424/5; 260/465 D
[58] Field of Search ..................... 260/465 D; 424/5

[56] References Cited

FOREIGN PATENT DOCUMENTS 1467994  3/1965  Fed. Rep. of Germany .............. 424/5

Primary Examiner—Frederick E. Waddell
Attorney, Agent, or Firm—Millen & White

[57] ABSTRACT

2,4,6-Triiodobenzonitriles of the formula

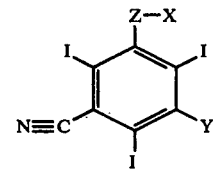

wherein Z is a direct bond or alkylene, X is —COOH or —NR₁R₂ wherein R₁ is H or hydrocarbon or hydroxyhydrocarbon and R₂ is lower acyl, and Y is H or —COOH, and their simple esters, amides and pharmaceutically acceptable salts, are useful as X-ray contrast agents and can be prepared by diazotizing the corresponding 2,4,6-triiodoanilines followed by reaction with a metal cyanide.

20 Claims, No Drawings

2,4,6-TRIIODOBENZONITRILE DERIVATIVES AND X-RAY CONTRAST MEDIA COMPRISING THEM

BACKGROUND OF THE INVENTION

This invention relates to novel 2,4,6-triiodobenzonitriles and to their use as X-ray contrast agents and to contrast media comprising them.

SUMMARY OF THE INVENTION

In a composition aspect, this invention relates to novel 2,4,6-triiodobenzonitrile derivatives of Formula I

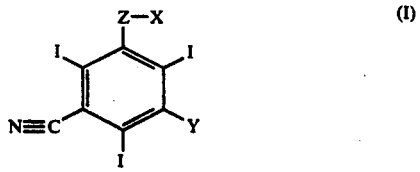

wherein Z is a direct bond or alkylene or alkenylene of up to 7 carbon atoms; X is —COOH or

wherein $R_1$ is a hydrogen atom or alkyl or hydroxy alkyl of up to 4 carbon atoms or a corresponding hydroxyalkyl group, and $R_2$ is the acyl radical of a hydrocarbon carboxylic acid of 2 to 5 carbon atoms or of a corresponding hydroxy carboxylic acid, and Y is a hydrogen atom or —COOH; and the physiologically acceptable salts with bases, and the corresponding esters and acid amides of the above compounds wherein at least one of X and Y are —COOH.

In another composition aspect, this invention relates to X-ray contrast media comprising one or more 2,4,6-triiodobenzonitriles of this invention.

In process aspects, this invention relates to methods of making and using the novel compositions of this invention.

DETAILED DISCUSSION

Contemplated compounds of this invention are those of Formula I wherein:

(a) Z is a direct single bond to which the X group is attached to the benzene ring;

(b) Z is a divalent saturated or unsaturated bridging alkylene group;

(c) Y is —COOH, including those of each of (a) and (b), above;

(d) physiologically acceptable salts of those of (c), above;

(e) X is —COOH, including those of each of (a) through (d), above, and the physiologically acceptable salts thereof;

(f) Y is H, including each of (a) through (d) above, and especially those of (c) and (d), above;

(g) an amide of an acid of (c) above, especially those wherein X is —COOH;

(h) an ester of an acid of (c) above, especially those wherein X is —COOH.

The acids of this invention, i.e., at least one of X and Y are —COOH, can be in the form of the physiologically acceptable salts thereof with bases. Suitable cations are all pharmaceutically acceptable cations, e.g., sodium, calcium, magnesium, and those of amines, e.g., alkanolamines, including ethanolamine, diethanolamine and N-methylglucamine.

When Z is a single bond linking X to the benzene ring and X is —COOH, the compounds of this invention are 5-cyano-2,4,6-triiodobenzoic acids (Y is H) and their salts, amides and esters, and 5-cyano-2,4,6-triiodoisophthalic acids (Y is —COOH), and their salts, mono- and di-amides and mono- and di-esters.

When Z is alkylene and X is —COOH, the compounds of this invention are 5-cyano-2,4,6-triiodophenalkanoic acids (Y is H) and the corresponding compounds bearing a —COOH group at the 3-position of the phenyl ring, and their salts, amides and esters.

When Z is a single bond linking X to the benzene ring and X is —NR$_1$R$_2$, the compounds of this invention are 5-cyano-2,4,6-triiodo-anilides (Y is H) and mon-amides of 5-cyano-2,4,6-triiodoisophthalic acids (Y is —COOH), and their salts, mono-esters and the corresponding diamides.

When Z is alkylene, it can be saturated or unsaturated and straight-chain or branched and can contain, e.g., 1–7 carbon atoms, and preferably is saturated alkylene of 1–4 carbon atoms. Examples of such alkylene groups are methylene, ethylene, propylene, isopropylene, isobutylene, —CH$_2$—CH(C$_2$H$_5$)— and —CH=C(C$_2$H$_5$)—.

When X is —NR$_1$R$_2$ and R$_1$ is lower alkyl, R$_1$ can be, e.g., of 1–4 carbon atoms and can be hydroxy substituted, preferably at the β- or γ-position. Examples of such groups are methyl, ethyl, propyl, butyl, β-hydroxypropyl and β-hydroxyethyl.

R$_2$ is the acyl radical of a simple carboxylic acid, e.g., an optionally hydroxy-substituted acyl radical of a hydrocarbon acid, preferably an alkanoic acid of 2–5 carbon atoms, e.g., acetyl, hydroxyacetal, propionyl, butyryl, lactyl. Contemplated equivalents are the acyl radical of higher such acids and of other carboxylic acids conventionally employed in pharmaceutical chemistry.

Included in the compounds of this invention are the simple esters of the free acids, i.e., compounds otherwise corresponding to Formula I wherein one or both of X and Y is a CO—OR group wherein R is, e.g., hydrocarbon of 1–4 carbon atoms, which optionally can be substituted by one or more hydroxy groups, e.g., methyl, ethyl, propyl, butyl and hydroxyethyl esters.

Also included in the compounds of this invention are the corresponding simple amides of the free acids of this invention, including those wherein the amide group is substituted, e.g., by hydrocarbon, preferably alkyl of 1–4 carbon atoms, which optionally can be substituted by one or more hydroxy groups and/or by a carbamoyl group.

Preferred such amides are compounds otherwise corresponding to Formula I wherein one or both of X and Y is an amide group of the formula CO—NR$_3$R$_4$ wherein R$_3$ and R$_4$ are alike or different and each represents a hydrogen atom or straight-chain or branched alkyl of 1–4 carbon atoms, or a corresponding alkyl group substituted by 1–3 hydroxy groups or a further amide group of the formula CO—NH—R$_5$ wherein R$_5$ is methyl or ethyl.

Specific examples of such R$_3$ and R$_4$ groups are methyl, ethyl, propyl, butyl, 2-hydroxyethyl, hydroxy-propyl, 2,3-dihydroxypropyl, 1,3-dihydroxypropyl, —CH₂—CO-NHCH₃ and

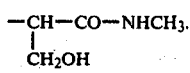

As stated above, included in the compounds of this invention are those otherwise corresponding to Formula I wherein both X and Y are alike or different and ester and amide groups.

The novel 2,4,6-triiodobenzonitrile derivatives are produced by diazotizing amino compounds of general Formula II

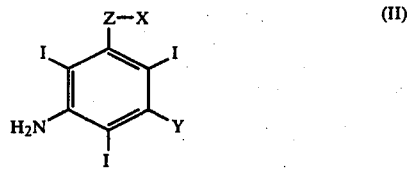

wherein X, Y and Z have the values given above, and then reacting the resultant product with a cyanide. The diazotization can be accomplished in the usual manner by reaction with a nitrite.

Advantageously, the diazotization is carried out under weakly acidic conditions, preferably in a pH range of 2-4, and with cooling, preferably at a temperature of from 0° to +10° C. Examples of suitable nitrites are alkali nitrites, e.g., sodium nitrite and potassium nitrite. The thus-produced diazonium salt can be separated or processed further immediately. Preferably, the diazonium salt is not isolated from the solution or suspension but instead is immediately further reacted with a cyanide, after bringing the mixture to pH 4–7 by the addition of a base, for example, sodium hydroxide, potassium hydroxide or ammonia.

The cyano group is introduced in accordance with methods known per se, for example, by the Sandmeyer reaction. In this process, the diazonium compound is reacted in the usual way with a cyanide complex, preferably a copper-cyanide complex salt. Especially suitable complex cyano compounds are, for example, K₂[Cu(CN)₃], K₃[Cu(CN)₄], K₂[CuNH₃(CN)₄] in an aqueous solution. The cyano group can be introduced at room temperature and at an elevated temperature, wherein temperatures of between 20° and 40° C. are considered to be preferred. Polar solvents are suitable for the reaction, e.g., water, N,N'-dimethylacetamide, N,N'-dimethylformamide, etc., and mixtures thereof, wherein the aqueous medium is preferred.

By replacing the amino group with the cyano group in compounds of Formula II, novel compounds of this invention are obtained which are distinguished by a good general physiological compatibility and especially a good neural compatibility, as can be seen from the data in Tables I and II.

With the claimed process for the manufacture of the new compounds of the formula I we succeeded for the first time in replacing the amino-group in triiodinated aniline derivates by a nitrilo group to introduce a substituent which is linked to the triiodinated aromatic nucleus via a C—C-bond.

TABLE 1

Compatibility after intravenous injection of the Na salt solutions (300 mg. iodine/ml., injection rate 2 ml./min.) with male and female (1:1) Wistar rats having a body weight of 90–110 g.; observation period: 7 days.

| Compound | Dosage g. iodine/kg. | Number of Animals | Number of Dead Animals |
|---|---|---|---|
| 5-Cyano-2,4,6-triiodo-isophthalic Acid | 3.0 | 4 | 0 |
| | 4.0 | 4 | 1 |
| | 6.0 | 4 | 4 |
| 5-Acetyl-amino-2,4,6-triiodoiso-phthalic Acid | 3.0 | 4 | 0 |
| | 4.0 | 4 | 1 |
| | 6.0 | 4 | 4 |

Table 1 shows, using 5-cyano-2,4,6-triiodoisophthalic acid as an example, that the compounds of this invention, after intravenous injection, show the same good compatibility as the conventional comparison compound.

TABLE 2

Neural compatibility after pericerebral injection of 0.04 ml. of the X-ray contrast media with variable concentration with male and female (1:1) Wistar rats; observation period: 24 hours.

| | | | Number of Animals with Symtoms: | | |
|---|---|---|---|---|---|
| Compound | Dosage mg. iodine/ kg. | Number of Animals | Anomalous Behavior Convulsions Death | Convulsions Death | Death |
| 5-Cyano-2,4,6-triiodo-isophthalic Acid | 10 | 10 | 2 | 1 | 0 |
| | 20 | 10 | 6 | 4 | 0 |
| | 40 | 10 | 10 | 10 | 1 |
| 5-Acetyl-amino-2,4,6-triiodo-isophthalic Acid | 5 | 10 | 3 | 2 | 0 |
| | 10 | 10 | 6 | 5 | 0 |
| | 20 | 10 | 9 | 9 | 3 |
| Amido-trizoic Acid | 5 | 10 | 2 | 2 | 0 |
| | 10 | 10 | 6 | 6 | 1 |
| | 20 | 10 | 9 | 9 | 5 |

It can be seen from Table 2 that the compounds of this invention are substantially less toxic than the conventional comparison compounds 5-acetylamino-2,4,6-triiodoisophthalic acid and amidotrizoic acid.

The compounds of this invention are suitable for use in X-ray contrast media for intravenous subarachnoid and oral applications, for example as urographics, angiographics, myelographics, cholegraphics, etc., e.g., in the same manner as the known 5-acetylamino-2,4,6-triiodoisophthalic acid and amidotrizoic acid.

The compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, viscous paraffin, perfume oil, fatty acid monoglycerides and diglycerides, pentaerythritol fatty acid esters, hydroxy methylcellulose, polyvinyl pyrrolidone, talc, etc.

For parenteral application, particularly suitable are solutions, preferably oily or aqueous solutions, as well as suspensions or emulsions. Ampoules are convenient unit dosages.

For enteral application, particularly suitable are tablets or dragees having talc and/or a carbohydrate carrier or binder or the like, the carrier preferably being lactose and/or corn starch and/or potato starch. A syrup or the like can be used wherein a sweetened vehicle is employed. Sustained release compositions can also be formulated wherein the active compound is protected with differentially degradable coatings, e.g., by microencapsulation, multiple coatings, etc.

For intravenous administration, the compounds of this invention are preferably used in aqueous solution whereby the concentration of active compound is between about 15% by volume and about 75% by volume. Generally the amount of active agent per unit dosage is about 5 to 50 g., preferably 7 to 35 g.

The solutions have a relative low viscosity and can be administered by intravenous injection and are furthermore distinguished by good circulatory compatibility and low toxicity.

The concentration of novel X-ray contrast media in an aqueous medium is entirely dependent on the roentgenographic method of diagnosis. Preferred concentrations and dosages of the novel compounds of this invention in the X-ray contrast media are concentrations of 30–450 mg. I/ml. Concentrations between 250 and 400 mg. I/ml. are particularly preferred. Preferred are dosages of 3–250 mg.

The compounds of this invention are also useful as intermediates for the preparation of other compounds suitable for use in X-ray contrast media. For example, the 5-cyano-3-acetylamino-2,4,6-triiodobenzoic acid can be reduced to 5-aminomethyl-3-acetylamino-2,4,6-triiodobenzoic acid, which is converted, by subsequent acetylation, into 5-acetylaminomethyl-3-acetylamino-2,4,6-triiodobenzoic acid (iodamide).

The selective reduction of the cyano group can be effected, for example, with a borane, at an elevated temperature. The iodamide, obtained by subsequent acetylation, is a commercial product.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

112 g. of 5-amino-2,4,6-triiodoisophthalic acid is suspended in 1100 ml. of water and dissolved by adding 10 g. of solution of caustic soda. The solution, which has a pH of 2.5, is then cooled to 0° C. and a solution of 20 g. of sodium nitrite in 60 ml. of water is added thereto. The pH is then adjusted down to 2.0 by adding drops of dilute sulfuric acid, and the batch is further stirred under constant ice cooling for 1 hour. By gradually adding dilute sodium hydroxide solution dropwise, the precipitated internal diazonium salt is dissolved at pH 4.5. In the meantime, a solution of 99 g. of copper(I) chloride and 172 g. of potassium cyanide in 800 ml. of water has been prepared and warmed to 30° C. The diazonium salt solution is added thereto all at once, under strong frothing. The reaction mixture is agitated for 15 minutes at 30° C. and then the copper salts are separated by acidifying the reaction solution to pH 3 with dilute sulfuric acid. The filtrate is brought to pH 0.5–1 by the further addition of dilute sulfuric acid, and the precipitate, after stirring in an ice bath for several hours, is vacuum-filtered, washed with water, and dried at 50° C. For purifying purposes, the reaction mixture is suspended in 400 ml. of water, dissolved by adding sodium hydroxide solution, and the solution is treated with 10 g. of activated carbon, allowed to remain for 30 minutes at room temperature under agitation, and then the filtrate is combined with an excess of a mineral acid. After stirring for several hours in an ice bath, the precipitate is vacuum-filtered, washed with water, and dried at 50° C. Yield: 89 g. (78% of theory) of 5-cyano-2,4,6-triiodoisophthalic acid as a white powder with a decomposition point of above 300° C.

EXAMPLE 2

(a) 1.12 g. of 5-amino-2,4,6-triiodoisophthalic acid is suspended in 15 ml. of water and dissolved by the dropwise addition of dilute sodium hydroxide solution at pH 2.5. Under ice cooling, a solution of 200 mg. of sodium nitrite in 1 ml. of water is added dropwise thereto. The batch is then brought back to pH 2.5 by adding dilute sulfuric acid, and further stirred for one hour in an ice bath. The thus-separated internal diazonium salt is vacuum-filtered, washed first with a small amount of ice-cold water and then with methanol, and gently dried under an argon vacuum. The product is a yellowish powder which turns to grey in a melting point tube at 110° C. under gas evolution and is found to split off iodine above 300° C.

(b) 2.65 g. of potassium cyanide is dissolved in 2.5 ml. of water; the solution is combined with 1.25 ml. of concentrated ammonia and then with a solution of 3.9 g. of copper(II) sulfate 5-hydrate in 250 ml. of water. The mixture is heated to 30° C. and at this point in time the diazonium salt solution, prepared according to (a) and brought to pH 5 with dilute sodium hydroxide solution, is added thereto. The yield is 82 g. (72% of theory) of 5-cyano-2,4,6-triiodoisophthalic acid, recrystallized from ethanol.

EXAMPLE 3

20.6 g. of 3-amino-2,4,6-triiodobenzoic acid is suspended in 220 ml. of water. After the dropwise addition of 24 ml. of a 30% aqueous sodium nitrite solution at 0° C., the pH value is brought down to 2 by adding dilute sulfuric acid. The batch is then stirred for one hour in an ice bath. By the gradual, dropwise addition of dilute sodium hydroxide solution, the batch is raised to pH 4.5, and the solution is allowed to stand under ice cooling. In the meantime, a solution of 20 g. of copper(I) chloride and 34 g. of potassium cyanide in 160 ml. of water has been prepared, warmed to 30° C., and the diazotization solution is added thereto all at once, under the occurrence of strong frothing. The mixture is stirred for another 15 minutes at 30° C. and then the copper salts are separated by acidifying the reaction solution to pH 3 with concentrated hydrochloric acid. The filtrate is brought to pH 0.5–1 by the further addition of concentrated hydrochloric acid, and the precipitate, after several hours of agitation in an ice bath, is vacuum-filtered and washed with water. The compound, moist from vacuum-filtering, is suspended in 50 ml. of water, dissolved by adding dilute sodium hydroxide solution, and the solution is treated by stirring with activated carbon and filtered to a clear state. By adding drops of concentrated hydrochloric acid, the solution is brought to pH 0.5–1 and then stirred for several hours in an ice bath; the precipitate is vacuum-filtered. After washing with acetone-containing water and drying at 50° C., 16 g. (76% of theory) of 3-cyano-2,4,6-triiodobenzoic acid is obtained as a white powder, m.p. 238°–240° C. (decomposition).

EXAMPLE 4

23.4 g. of 5-amino-2,4,6-triiodoisophthalic acid monomethylamide is suspended in 500 ml. of water and dissolved by the addition of dilute sodium hydroxide solution. The reaction solution is combined with 8 g. of sodium nitrite, cooled to 0° C., and such an amount of dilute sulfuric acid is slowly added dropwise that the pH is 2.0. The batch is stirred for 3 hours in an ice bath and neutralized by the gradual addition of concentrated ammonia. In the meantime, a solution of 20 g. of copper(I) chloride and 34 g. of potassium cyanide in 320 ml. of water has been prepared in the meantime, warmed to 30° C. The diazotization batch is added thereto all at once, during which step strong frothing occurs. The mixture is stirred for another 30 minutes at 30° C. and then the copper salts are separated by acidification with dilute hydrochloric acid to pH 4. The filtrate is brought to pH 1 by adding concentrated hydrochloric acid, and the reaction mixture is extracted with ethyl acetate. The ethyl acetate solution is washed with water, dried over sodium sulfate, and, after treatment with activated carbon, concentrated under reflux to dryness. The residue is suspended in 100 ml. of water and then dissolved extensively by adding dilute sodium hydroxide solution. After treating the aqueous solution with activated carbon, the filtrate is acidified with excess concentrated hydrochloric acid, and the precipitate is vacuum-filtered after several hours of agitation in an ice bath, washed with water, and dried at 50° C., thus obtaining 17 g. (72% of theory) of 5-cyano-2,4,6-triiodoisophthalic acid monomethylamide as a white powder having a decomposition point of above 300° C.

EXAMPLE 5

25.8 g. of 5-amino-2,4,6-triiodoisophthalic acid bis(2-hydroxyethyl)amide is dissolved under heating in 100 ml. of dimethylacetamide. The reaction solution is cooled in an ice bath and gently combined with approximately the same volume of water so that the compound remains dissolved. By the addition of a small amount of concentrated sulfuric acid, the batch is then brought to pH 2 and, under constant ice cooling, a solution of 4 g. of sodium nitrite in 12 ml. of water is added dropwise thereto within 30 minutes. After bringing the pH back to 2 by means of concentrated sulfuric acid, the batch is agitated for 3 hours in an ice bath. In the meantime, a solution of 20 g. of copper(I) chloride and 35 g. of potassium cyanide in 150 ml. of water has been prepared, warmed to 30° C. The diazonium salt solution, neutralized with dilute sodium hydroxide solution, is added all at once to the first-mentioned solution. The reaction mixture is agitated for another 15 minutes at 30° C. until the gas evolution has ceased, whereupon it is cooled to −10° C. and the batch is extracted with 500 ml. of ethyl acetate in incremental portions. The combined ethyl acetate extracts are rewashed several times with water, dried over sodium sulfate, and concentrated to about 50 ml. The compound is precipitated by the gradual addition of diisopropyl ether and, after several hours of agitation in an ice bath, the product is vacuum-filtered. Washing with diisopropyl ether and drying at 50° C. yields 18 g. (68% of theory) of 5-cyano-2,4,6-triiodoisophthalic acid bis(2-hydroxyethyl)amide having a decomposition point of above 300° C.

EXAMPLE 6

5.7 g. of β-(2,4,6-triiodo-3-aminophenyl)-α-ethylpropionic acid is dissolved in 20 ml. of concentrated sulfuric acid under agitation at room temperature. This solution is combined with 2 g. of finely pulverized sodium nitrite, added in incremental portions, after the solution has been cooled to 0° C. The batch is maintained at 5° C. for 2 hours under stirring. Subsequently 100 ml. of water is added dropwise to the reaction mixture under constant cooling in an ice bath, and the batch is brought to pH 7 by the dropwise addition of concentrated ammonia; during this step, the internal temperature is not to exceed 5° C. In the meantime, a solution of 5 g. of copper(I) chloride and 8.5 g. of potassium cyanide in 100 ml. of water has been prepared and warmed to 30° C. The diazotization batch is then added to this solution. The mixture is heated for 15 minutes to 30° C. until the gas evolution has ceased, and the mixture is decanted from the precipitated reaction product. The latter is taken up in 50 ml. of dilute sodium hydroxide solution, and the reaction solution is treated with activated carbon. The clear filtrate is decolorized by repeated extraction with activated carbon and is then brought to pH 3.5 with concentrated hydrochloric acid. The mixture is stirred for several hours, the precipitate is vacuum-filtered and dried at 50° C. Yield: 3.9 g. (68% of theory) of β-(2,4,6-triiodo-3-cyanophenyl-)α-ethylpropionic acid as a white powder with a melting point of 218°–220° C. (methanol).

EXAMPLE 7

30 g. of 2,4,6,-triiodo-5-amino-3-acetylaminobenzoic acid is suspended in 450 ml. of water and converted into a clear solution by adding concentrated sodium hydroxide solution. The reaction solution is cooled to 5° C. in an ice bath and brought to pH 2.5 by the dropwise addition of semiconcentrated sulfuric acid. Under ice cooling, a solution of 8 g. of sodium nitrite in 24 ml. of water is added dropwise to the thus-formed, fine suspension, and the pH is again set at 2.5 by the use of semiconcentrated sulfuric acid. After stirring for 2 hours in an ice bath, the batch is brought to pH 5 by the dropwise addition of dilute sodium hydroxide solution under constant cooling. The reaction mixture is then poured into a solution of 20 g. of copper(I) chloride and 33.4 g. of potassium cyanide in 80 ml. of water, warmed to 30° C. The batch is maintained for 2 hours at this temperature. Then, the reaction mixture is brought to pH 2 by adding concentrated hydrochloric acid; the thus-separated precipitate is vacuum-filtered and washed with water. The crude product, dried at 50° C., which still contains copper salts, is then treated twice with respectively 300 ml. of methanol; the insoluble proportions are separated, and the methanolic solution is extensively concentrated. After the addition of 100 ml. of water, the batch is brought to pH 11 by adding dilute sodium hydroxide solution, decolorized by repeatedly treating the solution with activated carbon, and the desired compound is precipitated by adding an excess of concentrated hydrochloric acid, washed with water, and dried at 50° C., thus obtaining 22.6 g. (75% of theory) of 2,4,6-triiodo-5-cyano-3-acetylaminobenzoic acid, m.p. 275°-278° C. (decomposition).

EXAMPLE 8

28 g. of 3-amino-5-acetylaminomethyl-2,4,6-triiodobenzoic acid is suspended in 450 ml. of water, and the suspension is combined dropwise with a solution of 4.5 g. of sodium nitrite in 24 ml. of water under cooling between 0° and +5° C. After setting a pH of 2.5 by the addition of dilute sulfuric acid, the batch is stirred for 2 hours in an ice bath. Under cooling, 30 ml. of a 30% sodium hydroxide solution is then added dropwise within one hour. In the meantime, a hot solution of 45 g. of copper(II) sulfate pentahydrate and 11.7 g. of sodium chloride in 160 ml. of water is combined with a solution of 9.6 g. of sodium bisulfite and 6.3 g. of caustic soda in 80 ml. of water and, after cooling, the freshly precipitated copper(I) chloride is vacuum-filtered. The latter is washed with water, suspended in 80 ml. of water, and dissolved by the addition of 30 g. of potassium cyanide. The diazotization batch is added thereto, and the mixture is stirred at +30° C. until the gas evolution has ceased. After the addition of 5 g. of urea, the copper salts are precipitated by adding glacial acetic acid, vacuum-filtered, and combined with concentrated hydrochloric acid, which latter is added dropwise until a pH of 1.8 has been reached. After several hours of agitation in an ice bath, the crude product is vacuum-filtered, washed with water, and dried. Recrystallization from 90% aqueous ethanol yields 20 g. (70% of theory) of 3-cyano-5-acetylaminomethyl-2,4,6-triiodobenzoic acid as a white powder, m.p. 271° C. (decomposition).

EXAMPLE 9

48.2 g of 5-amino-2,4,6-triiodoisophthalic acid mono-N-(2-hydroxyethyl)amide is suspended in 450 ml. of water. The suspension is cooled to 0° C. and, under constant cooling in an ice bath, a solution of 7 g. of sodium nitrite in 24 ml. of water is added dropwise thereto. Then, a pH of 2.5 is set by adding semiconcentrated sulfuric acid at 0°-5° C., and the mixture is agitated at this temperature for 2 hours. The batch is then neutralized by the dropwise addition of concentrated sodium hydroxide solution under ice bath cooling and poured, under vigorous agitation, into a solution of 35.8 g. of copper(I) cyanide and 66.8 g. of potassium cyanide in 320 ml. of water. After the evolution of gaseous nitrogen has ceased, the mixture is allowed to remain at room temperature under agitation and then brought to a pH of 3.5 by the dropwise addition of concentrated hydrochloric acid. The precipitated copper salts are vacuum-filtered, and the filtrate is brought to pH 0.2 by further acidification. After several hours of stirring in an ice bath, the precipitate is vacuum-filtered, washed with water, and dried at 60° C., thus obtaining 43.8 g. (=94.8% of theory) of 5-cyano-2,4,6-triiodoisophthalic acid mono-N-(2-hydroxyethyl)amide having a decomposition point of above 300° C.

EXAMPLE 10

Analogously to Example 9, 44.6 g. of 5-amino-2,4,6-triiodoisophthalic acid monoamide yields 37.4 g. (=82% of theory) of 5-cyano-2,4,6-triiodoisophthalic acid monoamide having a decomposition point of above 300° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

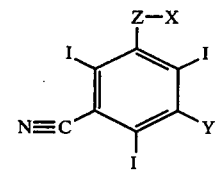

wherein Z is a direct bond or alkylene or alkenylene of up to 7 carbon atoms; X is —COOH or

wherein $R_1$ is a hydrogen atom or alkyl or hydroxy alkyl of up to 4 carbon atoms or a corresponding hydroxy alkyl group, and $R_2$ is the acyl radical of a hydrocarbon carboxylic acid of 2 to 5 carbon atoms or of a corresponding hydroxy carboxylic acid, and Y is a hydrogen atom or —COOH; and the physiologically acceptable salts with bases, and the corresponding esters and acid amides of the above compounds wherein at least one of X and Y is (a) of the formula —CO—OR wherein R is hydrocarbon of 1–4 carbon atoms or a corresponding hydrocarbon group substituted by one or more hydroxy groups, or (b) of the formula —CO—NR$_3$—R$_4$ wherein R$_3$ and R$_4$ each is a hydrogen atom or alkyl of 1–4 carbon atoms or corresponding alkyl substituted by 1–3 hydroxy groups, or (c) of the formula —CO—NH—R$_5$ wherein R$_5$ is methyl or ethyl.

2. A compound of claim 1 wherein Y is H.
3. A compound of claim 1 wherein Y is —COOH.
4. A compound of claim 1 wherein wherein Z is a direct bond.
5. A compound of claim 4 wherein X is —NR$_1$R$_2$.
6. A compound of claim 5 wherein R$_1$ is a hydrogen atom.
7. A compound of claim 1 wherein Z is alkylene of up to 4 carbon atoms.
8. A compound of claim 7 wherein X is —NR$_1$R$_2$.
9. A compound of claim 8 wherein R$_1$ is a hydrogen atom.
10. 5-Cyano-2,4,6-triiodoisophthalic acid, a compound of claim 1.
11. 5-Cyano-2,4,6-triiodoisophthalic acid monomethylamide, a compound of claim 1.
12. 5-Cyano-2,4,6-triiodoisophthalic acid bis(2-hydroxyethyl)amide, a compound of claim 1.
13. 5-Cyano-2,4,6-triiodobenzoic acid, a compound of claim 1.
14. β-(2,4,6-Triiodo-3-cyanophenyl-)α-ethylpropionic acid, a compound of claim 1.
15. 5-Cyano-3-acetylamino-2,4,6-triiodobenzoic acid, a compound of claim 1.
16. 3-Cyano-5-acetylaminomethyl-2,4,6-triiodobenzoic acid, a compound of claim 1.

17. 5-Cyano-2,4,6-triiodoisophthalic acid mono-N-(2-hydroxyethyl)amide, a compound of claim 1.

18. 5-Cyano-2,4,6-triiodoisophthalic acid monoamide, a compound of claim 1.

19. An X-ray contrast agent adapted for oral or intravenous administration comprising a radiopaque amount per unit dosage of a compound of claim 1, in admixture with a pharmaceutically acceptable carrier.

20. A method for conducting a radiological examination of a patient which comprises administering systemically thereto prior to examination a radiopaque amount of a compound of claim 1.

* * * * *